(12) United States Patent
Cogill et al.

(10) Patent No.: US 10,278,634 B2
(45) Date of Patent: May 7, 2019

(54) DETECTING AND EXPLAINING DRIVER CONFIDENCE

(71) Applicant: INTERNATIONAL BUSINESS MACHINES CORPORATION, Armonk, NY (US)

(72) Inventors: Randall L. Cogill, Dublin (IE); Freddy Lecue, Dublin (IE); Joe Naoum-Sawaya, London (CA); Robert Shorten, Mulhuddart (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/293,501

(22) Filed: Oct. 14, 2016

(65) Prior Publication Data
US 2018/0103888 A1    Apr. 19, 2018

(51) Int. Cl.
| | |
|---|---|
| *A61B 5/18* | (2006.01) |
| *A61B 5/0205* | (2006.01) |
| *A61B 5/00* | (2006.01) |
| *A61B 5/021* | (2006.01) |
| *A61B 5/024* | (2006.01) |
| *G01C 21/34* | (2006.01) |
| *A61B 5/053* | (2006.01) |

(52) U.S. Cl.
CPC .............. *A61B 5/18* (2013.01); *A61B 5/0205* (2013.01); *A61B 5/6893* (2013.01); *A61B 5/7246* (2013.01); *G01C 21/3415* (2013.01); *G01C 21/3484* (2013.01); *G01C 21/3492* (2013.01); *A61B 5/021* (2013.01); *A61B 5/024* (2013.01); *A61B 5/0531* (2013.01); *A61B 2560/0242* (2013.01)

(58) Field of Classification Search
None
See application file for complete search history.

(56) References Cited

U.S. PATENT DOCUMENTS

| | | | |
|---|---|---|---|
| 5,835,008 A * | 11/1998 | Colemere, Jr. ........ | B60Q 1/441 340/349 |
| 8,010,283 B2 | 8/2011 | Yoshida et al. | |
| 8,297,977 B2 | 10/2012 | Freund | |
| 8,483,909 B2 | 7/2013 | Visconti et al. | |
| 8,577,703 B2 | 11/2013 | McClellan et al. | |
| 2003/0097047 A1 * | 5/2003 | Woltermann ......... | A61B 5/165 600/300 |

(Continued)

FOREIGN PATENT DOCUMENTS

JP    2006172012 A    6/2006

OTHER PUBLICATIONS

Rittger et al., "Driving behaviors at traffic light intersections," Cognition Technology & Work, v. 17, n. 4, 2015 (26 pages).

*Primary Examiner* — Mussa A Shaawat
*Assistant Examiner* — Abdhesh K Jha
(74) *Attorney, Agent, or Firm* — Griffiths & Seaton PLLC

(57) ABSTRACT

Embodiments for driver confidence evaluation while operating a vehicle by a processor. Driver confidence, based upon one or more psychophysical parameters of a driver, is combined and correlated with a plurality of environmental factors and route information. A confidence in vehicular operational capabilities of the driver may be detected according to the correlation.

15 Claims, 12 Drawing Sheets

(56) References Cited

U.S. PATENT DOCUMENTS

| | | |
|---|---|---|
| 2013/0041521 A1 | 2/2013 | Basir et al. |
| 2013/0079602 A1 | 3/2013 | Picard et al. |
| 2015/0345981 A1 | 12/2015 | Goldman-Shenhar et al. |
| 2017/0364070 A1* | 12/2017 | Oba .................... G05D 1/0061 |
| 2018/0032072 A1* | 2/2018 | Hoye ................... G05D 1/0061 |

* cited by examiner

DETECTING AND EXPLAINING DRIVER CONFIDENCE

BACKGROUND OF THE INVENTION

Field of the Invention

The present invention relates in general to computing systems, and more particularly to, various embodiments for driver confidence evaluation while operating a vehicle by a processor.

Description of the Related Art

In today's interconnected and complex society, computers and computer-driven equipment are more commonplace. Processing devices, with the advent and further miniaturization of integrated circuits, have made it possible to be integrated into a wide variety of personal, business, health, home, education, and other devices. Accordingly, the use of computers, network appliances, and similar data processing devices continue to proliferate throughout society.

SUMMARY OF THE INVENTION

Various embodiments for driver capability, ability, confidence, and/or competency evaluation while operating a vehicle by a processor, are provided. In one embodiment, by way of example only, a method for driver capability evaluation while operating a vehicle, again by a processor, is provided. Driver confidence, based upon one or more psychophysical parameters of a driver, is combined and correlated with a plurality of environmental factors and route information. A confidence in vehicular operational capabilities of the driver may be detected according to the correlation.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
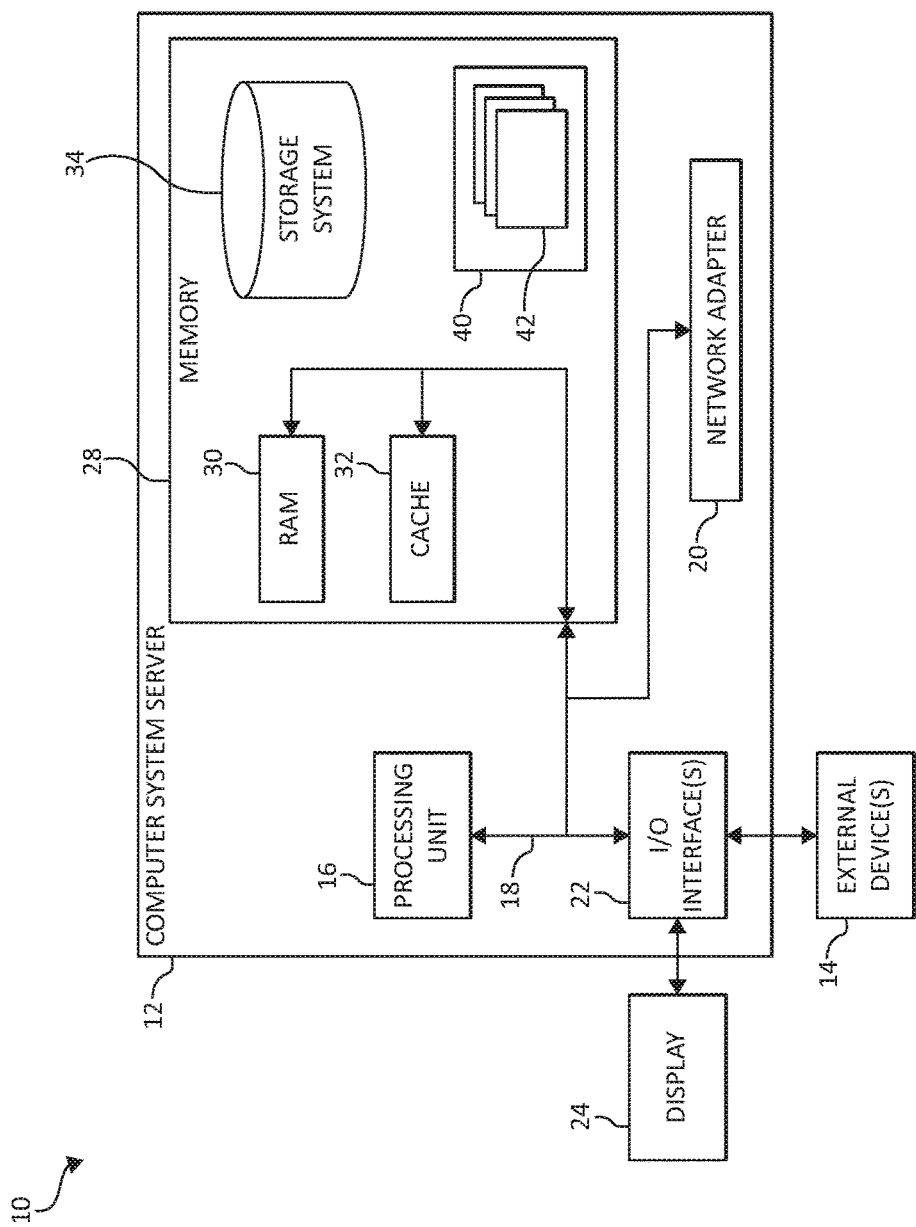
FIG. 1 is a block diagram depicting an exemplary computing node according to an embodiment of the present invention.

Rapid growth in various municipalities, cities, and other communities result in increased infrastructures such as, for example, roads, bridges, and/or buildings. The complexity of these infrastructures often times create challenges for individuals, such as operators of vehicles, to safely navigate through these complex environments. Adding to these challenges, a wide variety of other factors that can affect an operator of a vehicle to safely and securely operate a vehicle, particularly when skill sets for vehicle operations differ between various operators. More specifically, the skill sets for vehicle operations depend on the ability and driving experience of each operator and on the various psychophysical conditions.

For example, the more complex an infrastructure and environment is the more anxious various vehicle operators may become, even when equipped with a complex navigation system. Consequently, the deterioration of the psychophysical conditions may increase the driver's confidence (e.g., driver anxiety level), leading to dangerous driving conditions and accidents caused by the joint effect of road complexity, environmental conditions, and/or anxiety. Accordingly, depending on a driver's skill set for vehicle operations, some drivers may not be prepared to operate a vehicle in each of the various types of travel routes having varying degrees of complexity under any environmental (e.g., weather, time of day or year, or traffic) conditions. For example, some vehicle operators may be relaxed on primarily straight roads in the daylight hours, while having extremely high degrees of stress when operating a vehicle in harsh weather conditions while driving on narrow roads during late night hours.

In view of the foregoing, the mechanisms of the present embodiment automatically detect the various types of travel routes having varying degrees of complexity under any environmental (e.g., weather, time of day or year, or traffic) conditions and patterns. In one aspect, a driver profile may be created with driver confidence with a road profile and other external data considered to evaluate driver's deficiencies. External information such as, for example weather, time of day, and time of season, may also be considered with the psychophysical conditions (e.g., driver anxiety) of the driver when computing a driver profile for evaluating driver competence. In one aspect, the complexity of a route associated, together with the environmental factors, may be used to detect and evaluate the driver competence. One or more travel routes may be determined as forbidden or restricted that may not be compliant with a driver's capability. That is, one or more warnings or suggestions may be provided alerting a driver of the travel routes that may not be compliant or compatible with a driver's skill set given the road complexity, driver's profile, and/or environmental factors. One or more suggestions or notifications may be provided to correct or improve a driver's capability, ability, confidence, and/or competency evaluation, improve driver confidence, and indirectly help improve driver health and more generally reduce traffic accidents.

In one embodiment, by way of example only, a method for driver capability, ability, confidence, and/or competency evaluation while operating a vehicle, again by a processor, is provided. Driver confidence (and/or driver anxiety), based upon one or more psychophysical parameters of a driver, is correlated with a plurality of environmental factors and route information. A capability, ability, confidence, and/or competency evaluation in vehicular operational capabilities of the driver may be detected according to the correlation.

In an additional aspect, the mechanisms of the present embodiment evaluate driver competence (e.g., a driver skill competence) by correlating user confidence (when operating a vehicle) with external data such as, for example, road information, street information, traffic information, weather data, time of day, and/or time of season. Detection of driver competence may be based on a confidence level (e.g., anxiety level) of one or more psychophysical characteristics or parameters (e.g., electro dermal activity, heart rate, blood pressure, etc.). A driver competence explanation may be provided that may be based on correlation of confidence and the external data.

The mechanisms of the illustrated embodiments leverage a variety of what will herein be referred to as "instrumentation" and/or other sensor, data-collection devices that are installed in electrical, electromechanical, electromagnetic, signal, or other communication with a particular vehicle component, such as vehicle parts, which may be used to monitor, measure, and/or collect one or more psychophysical characteristics or parameters. The instrumentation is used to evaluate driver competence and detect the one or more psychophysical characteristics or parameters (e.g., driver confidence or driver anxiety). If driver anxiety is detected, the instrumentation and other sensory devices then capture data from the vehicle component, which is supplied to a data repository for driver competence evaluation.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. As will be described, functional components of node 10 may even be miniaturized to the extent that they are integrated into wearable components to accomplish various purposes of the illustrated embodiments, such as into headgear, glasses, lenses, contacts, or other wearable components. Cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

In the context of the present invention, and as one of skill in the art will appreciate, various components depicted in FIG. 1 may be integrated into wearable components. For example, some of the processing and data storage capabilities associated with mechanisms of the illustrated embodiments may take place locally via local processing components, while the same components are connected via a network to remotely located, distributed computing data processing and storage components to accomplish various purposes of the present invention. Again, as will be appreciated by one of ordinary skill in the art, the present illustration is intended to convey only a subset of what may be an entire connected network of distributed computing components that accomplish various inventive aspects collectively.

Figure 2:
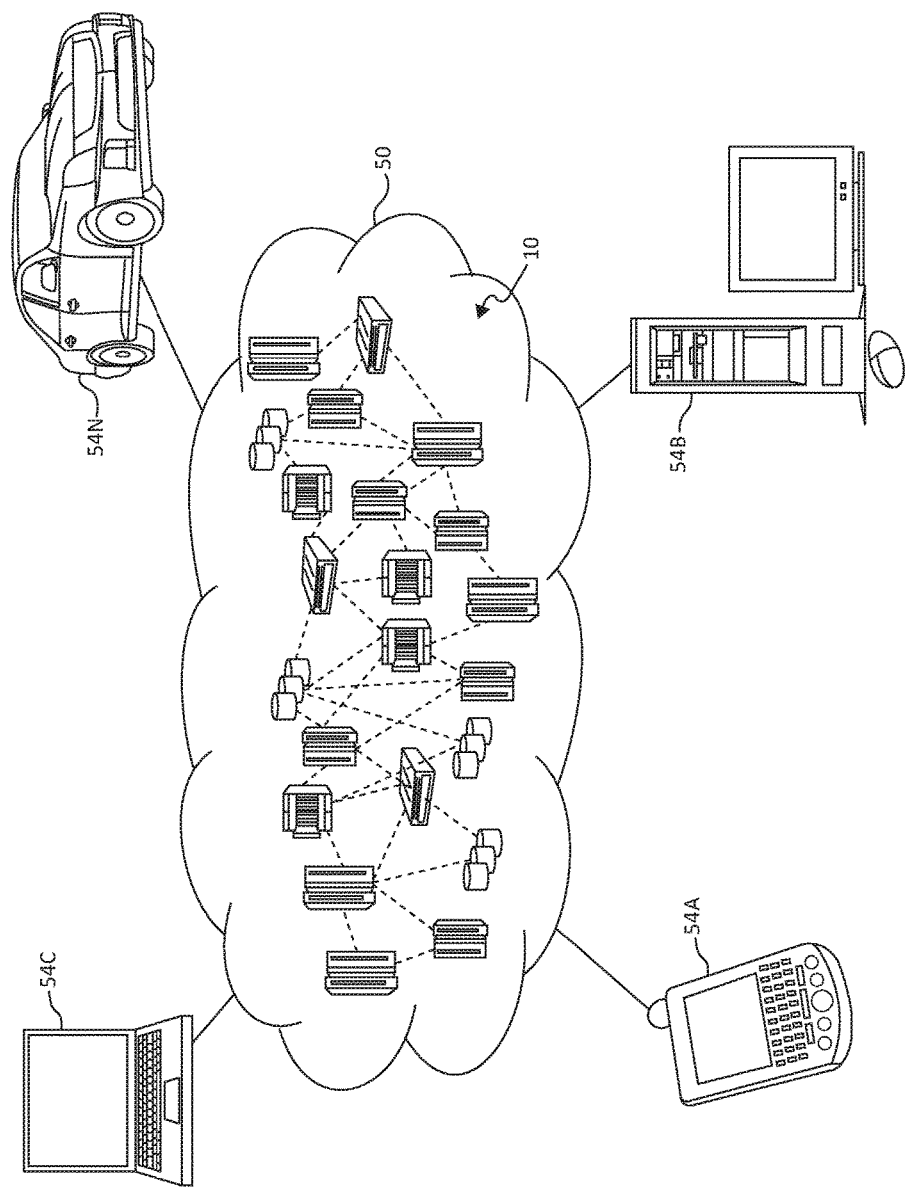
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, smartphone or cellular telephone 54A, desktop computer 54B, laptop computer 54C, and/or in the context of the present invention, vehicle 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
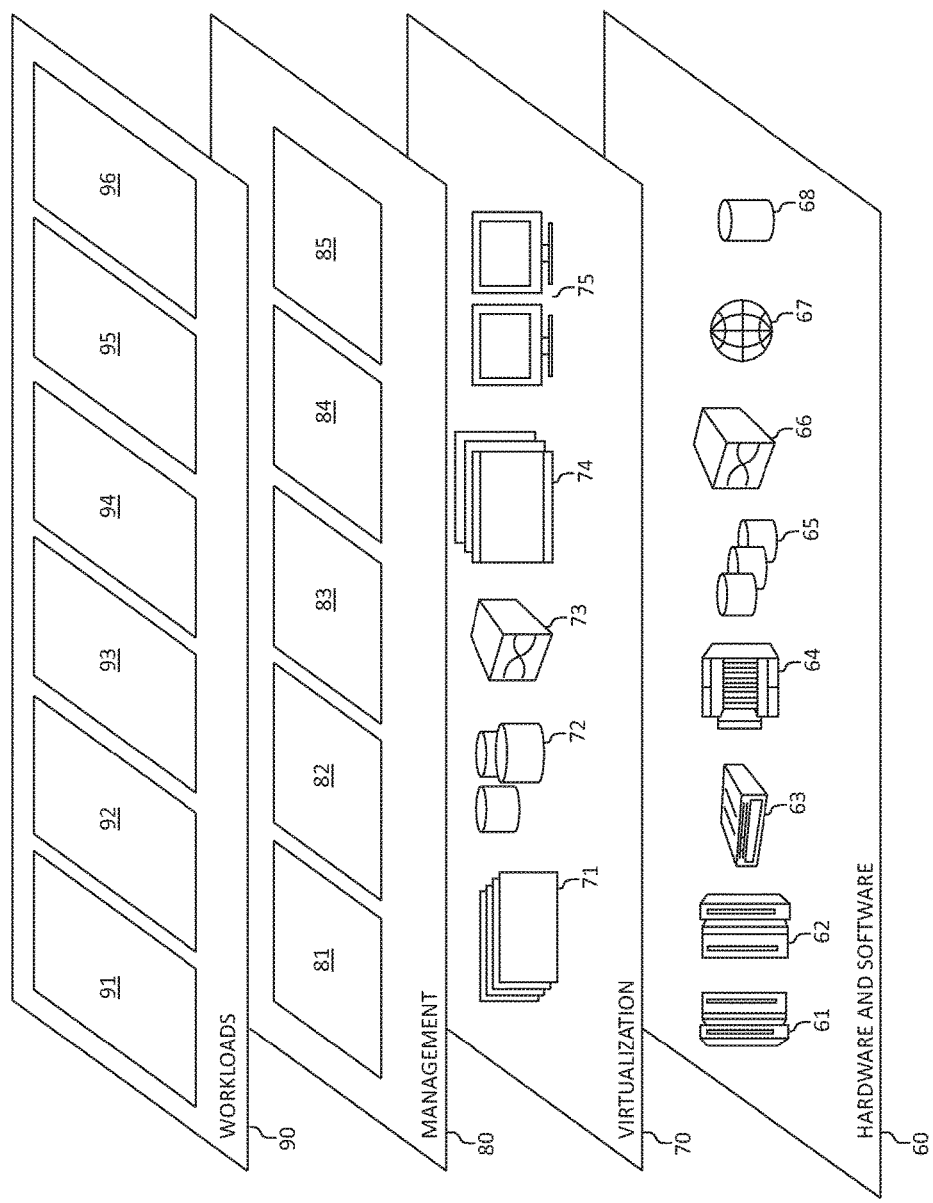
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various vehicle event data processing workloads and functions 96. In addition, driver competence evaluation workloads and functions 96 may include such operations as data analysis (including data collection and processing from various sensors) and data sharing workloads (such as sharing visual information over a network to another user). One of ordinary skill in the art will appreciate that the driver competence evaluation data processing workloads and functions 96 may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for driver competence detection and evaluation while operating a vehicle by a processor. In one embodiment, by way of example only, a method for driver competence evaluation while operating a vehicle, again by a processor, is provided. Driver confidence, based upon one or more psychophysical parameters of a driver, is correlated with a plurality of environmental factors and route information. A competence in vehicular operational capabilities of the driver may be detected according to the correlation.

Figure 4:
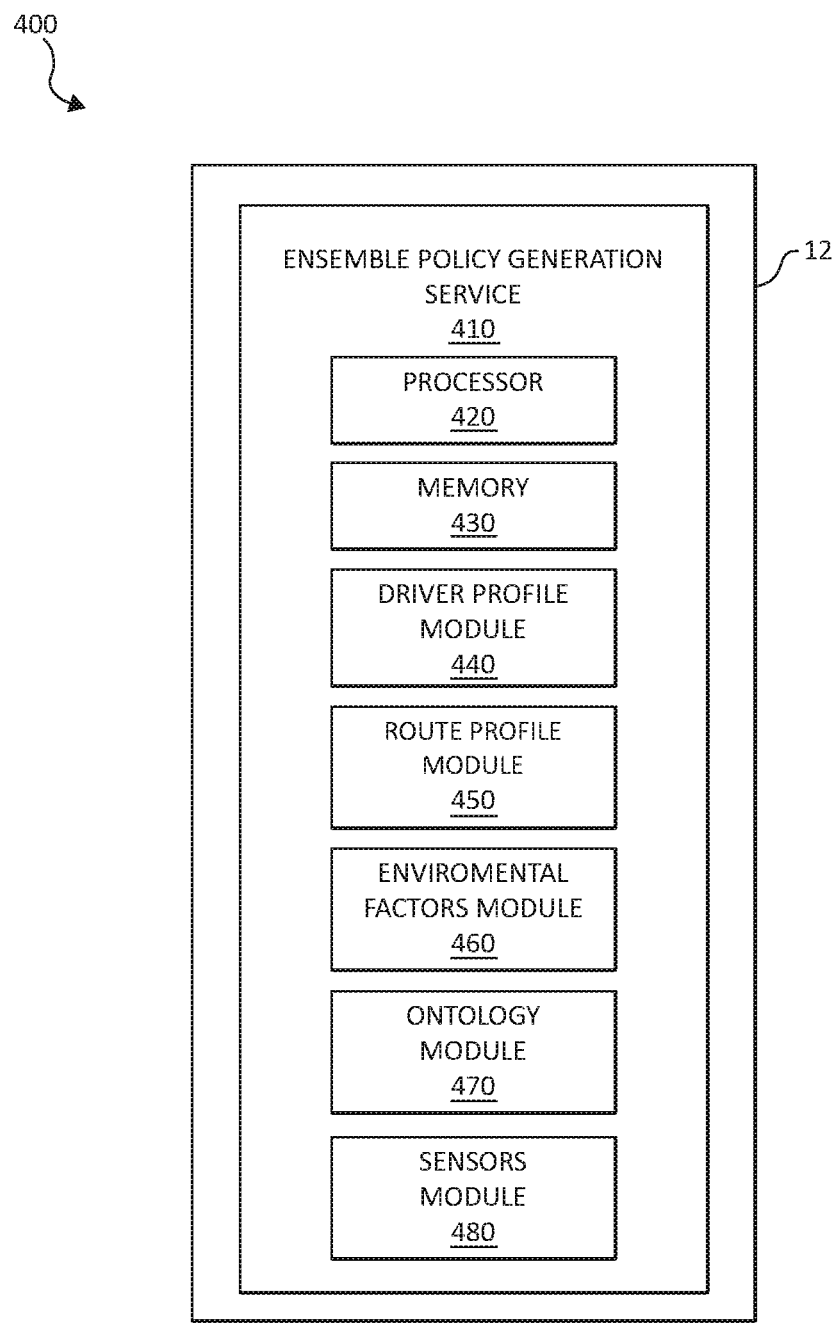
FIG. 4 is an additional block diagram depicting various user hardware functioning in accordance with aspects of the present invention.

Turning now to FIG. 4, a block diagram depicting exemplary functional components 400 according to various mechanisms of the illustrated embodiments, is shown. In one aspect, one or more of the components, modules, services, applications, and/or functions described in FIGS. 1-3 may be used in FIG. 4. An ensemble policy generation service 410 is shown, incorporating processing unit 420 to perform various computational, data processing and other functionality in accordance with various aspects of the present invention. The processing unit 420 may be in communication with memory 430. A driver profile module 440, route profile module 450, an environmental factors module 460, an ontology module 470 of a knowledge domain, and a sensors module 480 is shown.

As one of ordinary skill in the art will appreciate, the depiction of the various functional units in ensemble policy generation service 410 is for purposes of illustration, as the functional units may be located within the ensemble policy generation service 410 or elsewhere within and/or between distributed computing components. The ontology module 470 may include a knowledge domain or data and meta-data repository of routes, roads, streets, highways, interstates, bridges, maps, and/or a variety of infrastructures relating to travel each having information relating to both size, length, a degree of complexity or difficulty (e.g., travel navigation complexity), visibility, problems or issues relating to road work or repair, and/or traffic congestion.

The driver profile module 440, the route profile module 450, and the environmental factors module 460 may each work in concert with processing unit 420 and memory 430 to accomplish various aspects of the present invention, such as, for example creating a driver profile in the driver profile module 440 from correlating driver confidence (or driver anxiety), based upon one or more psychophysical parameters of a driver, with a plurality of environmental factors of the environmental factors module 460 and route information of the route profile module 450. In one aspect, the sensors module 480 may include one or more sensors for monitoring, collecting, and/or measuring one or more psychophysical characteristics and/or parameters.

For example, the sensors module 480, employing one or more sensors (which may be included in and/or associated with the driver and/or vehicle) may monitor, record, collect, and/or measure a number of psychophysical driver parameters by means of respective sensors (e.g., one or more biometric sensors, psychometric sensors, road sensors, traffic sensors, environmental sensors, vehicular sensors, inductive loop sensors, and/or electro dermal sensors) to evaluate and detect a driver's confidence condition as a function of the psychophysical parameters recorded by the sensors. Data collected by the sensors module 480 may be stored in the driver profile module 440, the route profile module 450, and/or the environmental factors module 460.

Using the driver profile module 440, the route profile module 450, and the environmental factors module 460, the ensemble policy generation service 410 detects a competence (e.g., a skill level taking into account age, experience, physical capabilities, physical limitations, and/or vehicle operational standards, such as, for example, vehicle operation standards as defined by governmental, educational institutions, and/or one or more vehicle safety regulation agencies or entities, organizations, and/or businesses) in vehicular operational capabilities of the driver according to the correlation.

The driver profile module 440, the route profile module 450, and the environmental factors module 460 may each undergo various data analytics functions associated with the ensemble policy generation service. As one of ordinary skill in the art will appreciate, the driver profile module 440, the route profile module 450, and the environmental factors module 460 may implement mathematical modeling, probability and statistical analysis or modeling, machine reasoning, probabilistic logic, text data compression, or other data processing technologies to carry out the various mechanisms of the illustrated embodiments. In one aspect, calculations may be performed using various mathematical operations or functions that may involve one or more mathematical operations (e.g., using addition, subtraction, division, multiplication, standard deviations, means, averages, percentages, statistical modeling using statistical distributions, by finding minimums, maximums or similar thresholds for combined variables, etc.).

In one aspect, a thesaurus or ontology as the knowledge domain, relating to the ontology module 470, may be used for the driver competence detection and evaluation with the information and concepts relating to routes, roads, streets, highways, interstates, bridges, maps, and/or a variety of infrastructures relating to travel each having information relating to both size, length, a degree of complexity or difficulty (e.g., travel navigation complexity), visibility, problems or issues relating to road work or repair, and/or traffic congestion. In one aspect, the ontology module 470 may be in association with one or more various applications, which may continuously provide updated information for the ontology. The thesaurus and ontology may also be used to assist with semantic correlating driver confidence, based upon one or more psychophysical parameters of a driver, with a plurality of environmental factors and route information and detecting a competence in vehicular operational capabilities of the driver according to the correlation.

In one aspect, the term "domain" is a term intended to have its ordinary meaning. In addition, the term "domain" can include an area of expertise for a system or a collection of material, information, content and/or other resources related to a particular subject or subjects. For example, a domain can refer to information and concepts relating to routes, roads, streets, highways, interstates, bridges, maps, and/or a variety of infrastructures relating to travel each having information relating to both size, length, a degree of complexity or difficulty (e.g., travel navigation complexity), visibility, problems or issues relating to road work or repair, and/or traffic congestion information. A domain can refer to information related to any particular subject matter or a combination of selected subjects.

The term ontology is also a term intended to have its ordinary meaning. In one aspect, the term ontology in its broadest sense may include anything that can be modeled as ontology, including but not limited to, taxonomies, thesauri, vocabularies, and the like. For example, an ontology may include information or content relevant to a domain of interest or content of a particular class, concept and/or property. Content can be any searchable information, for example, information distributed over a computer-accessible network, such as the Internet. A concept can generally be classified into any of a number of concepts which may also include one or more sub-concepts, all potentially connected with other concepts via properties defined in the ontology. Examples of concepts may include, but are not limited to, information and concepts relating to routes, roads, streets, highways, interstates, bridges, maps, and/or a variety of infrastructures relating to travel each having information relating to both size, length, a degree of complexity or difficulty (e.g., travel navigation complexity), visibility, problems or issues relating to road work or repair, and/or traffic congestion, information about individual people, cultures, groups, sociological groups, market interest groups, institutions, universities, governments, teams, or any other information group. The ontology can be continuously updated with the information synchronized with the sources, adding information from the sources to the ontology as models, attributes of models, or associations between models within the ontology.

In one aspect, the various functional units in ensemble policy generation service 410 analysis may apply to one or more heuristics and machine learning based models using a wide variety of combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting examples of temporal difference learning may include Q-learning and learning automata. Specific details regarding any of the examples of supervised, unsupervised, temporal difference or other machine learning described in this paragraph are known and are considered to be within the scope of this disclosure.

Figure 5:
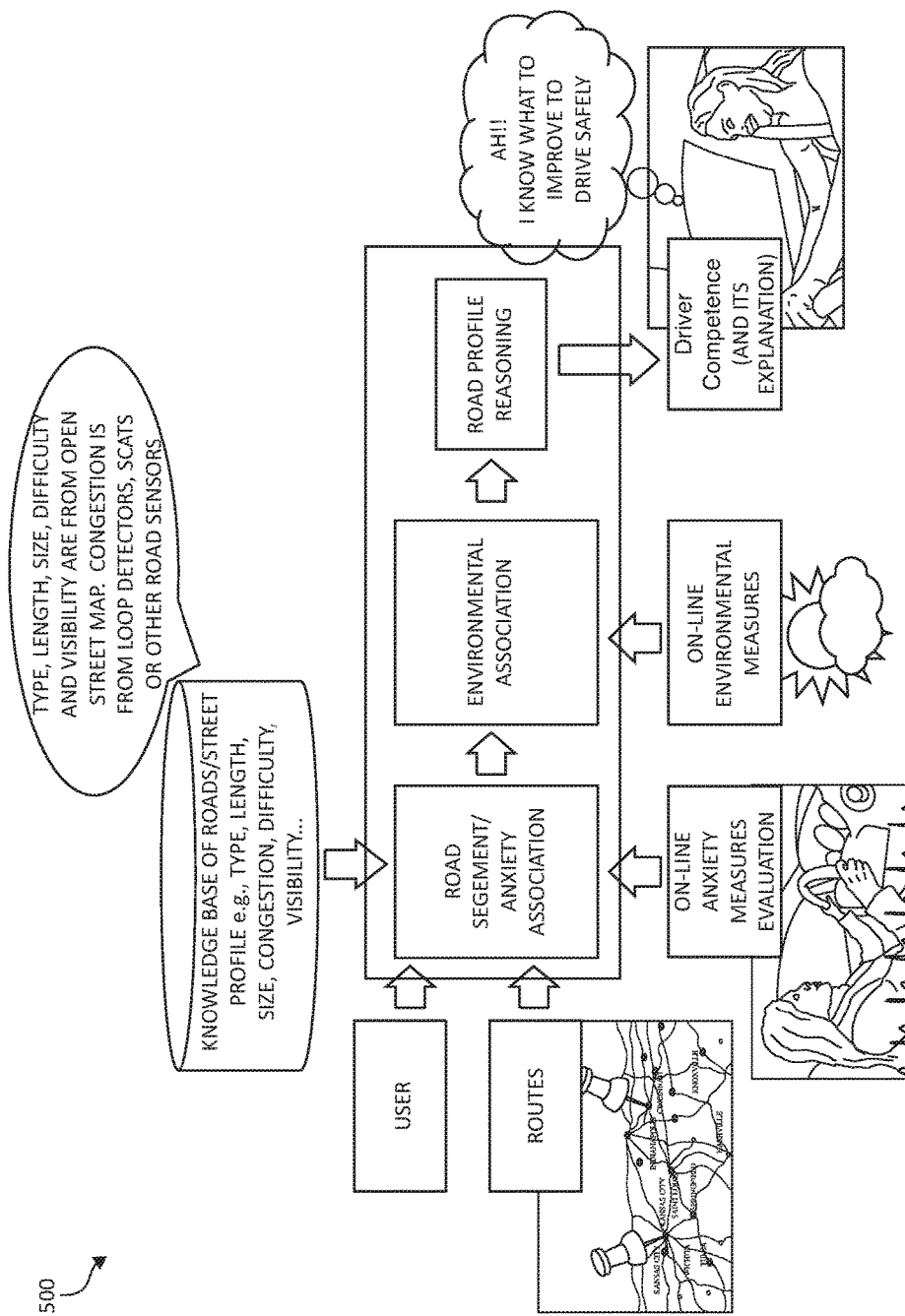
FIG. 5 is an additional block diagram depicting an exemplary functional relationship between various aspects of the present invention.

FIG. 5 is an additional block diagram depicting an exemplary functional relationship between various aspects of the present invention. As shown, the various blocks of functionality are depicted with arrows designating the blocks' 500 relationships with each other and to show process flow. Additionally, descriptive information is also seen relating each of the functional blocks 500. As will be seen, many of the functional blocks may also be considered "modules" of functionality, in the same descriptive sense as has been previously described in FIG. 4. With the foregoing in mind, the module blocks 500 may also be incorporated into various hardware and software components of a system for image enhancement in accordance with the present invention. Many of the functional blocks 500 may execute as background processes on various components, either in distributed computing components, or on the user device, or elsewhere, and generally unaware to the user performing generalized tasks of taking a picture with their camera. In one aspect, user (e.g., a driver) information, route information, and/or a knowledge domain of roads having a route (or street) profile (e.g., a route type, route length, route congestion, route difficulty, and/or route visibility) may be correlated together with on-line anxiety data that is measured and evaluated to form a road segment and anxiety association. In one aspect, the knowledge domain may use Sydney coordinated adaptive traffic system (SCATS) having one or more inductive loop sensors to detect vehicles approaching junctions and make an estimate of the state on the road. The SCATS may use the estimate to select a fixed timing plan from a look-up table of pre-designed plans. SCATS may allow for the coordination of adjacent junctions (offsets) and/or provide congestion information from loop detectors or other road detectors.

Having correlated the route information, user information, and a knowledge domain of roads with measured driver confidence information (e.g., driver anxiety information), on-line environmental measurements may also be correlated to form an environmental association with the road segment and anxiety association. Logic may be used to create a road profile with associated reasoning to evaluate and detect a driver competence. An explanation may be provided with the driver competence. In one aspect, the explanation and detection of the driver competence may provide one or more suggestions to decrease the driver's anxiety level and/or correct the detected competence of the driver (e.g., user may then know how to improve driver safety). In this way, the explanation and detection of the driver competence may provide joint information of driver anxiety with a road profile of computed routes. The explanation and detection of the driver competence may include providing an explanation of at least one suggestion to lower the driver anxiety or correct the competence in the vehicular operational capabilities (and/or providing at least one suggestion to increase the driver confidence or correct the confidence in the vehicular operational capabilities), provide customized travel routes for the driver to reduce the driver anxiety, and/or provide information relating to travel routes that may increase the driver's anxiety thereby warning the driver to seek an alternative route from these restricted or forbidden routes as they relate to the skill set of the driver. It should be noted that driver confidence may be a measure of driver anxiety which may reflect one or more psychophysical parameters of a driver.

FIGS. 6A-6F are additional block diagrams depicting an exemplary system for driver competence evaluation while operating a vehicle in accordance with various embodiments of the present invention. In one aspect, the present description will introduce six possible embodiments of explanation and detection of the driver competence that accomplish various aspects of the present invention as follows.

Figure 6A:
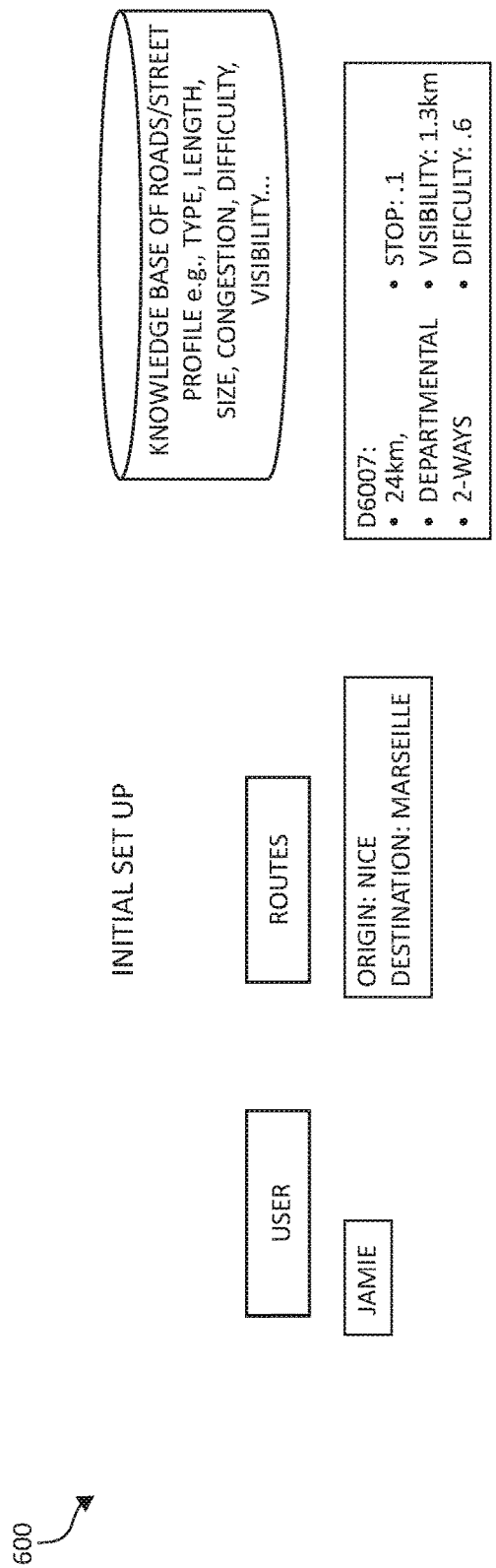
FIGS. 6A-6F are additional block diagrams depicting an exemplary system for driver confidence evaluation while operating a vehicle in accordance with various embodiments of the present invention.
Figure 6B:
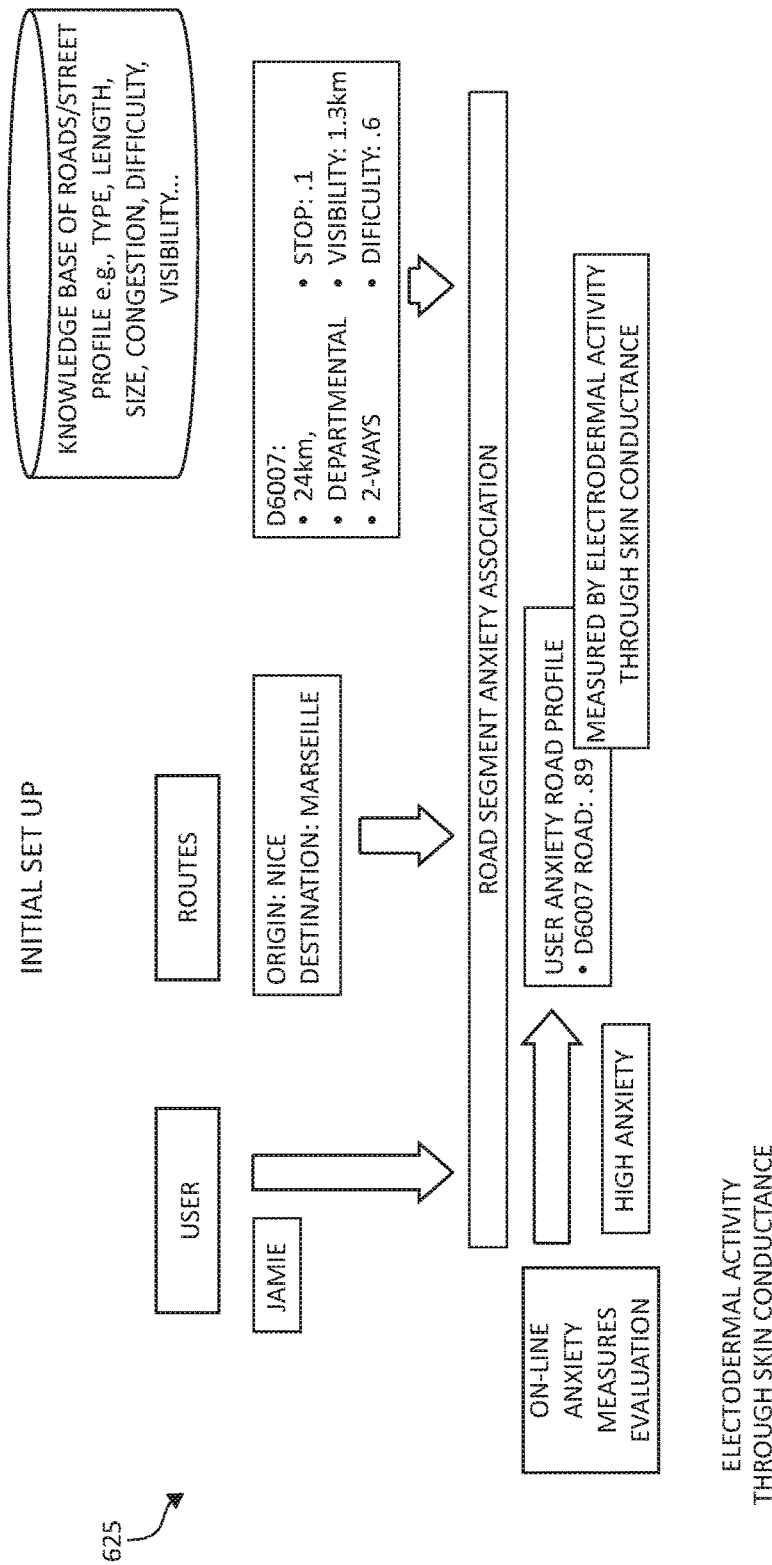
Figure 6C:
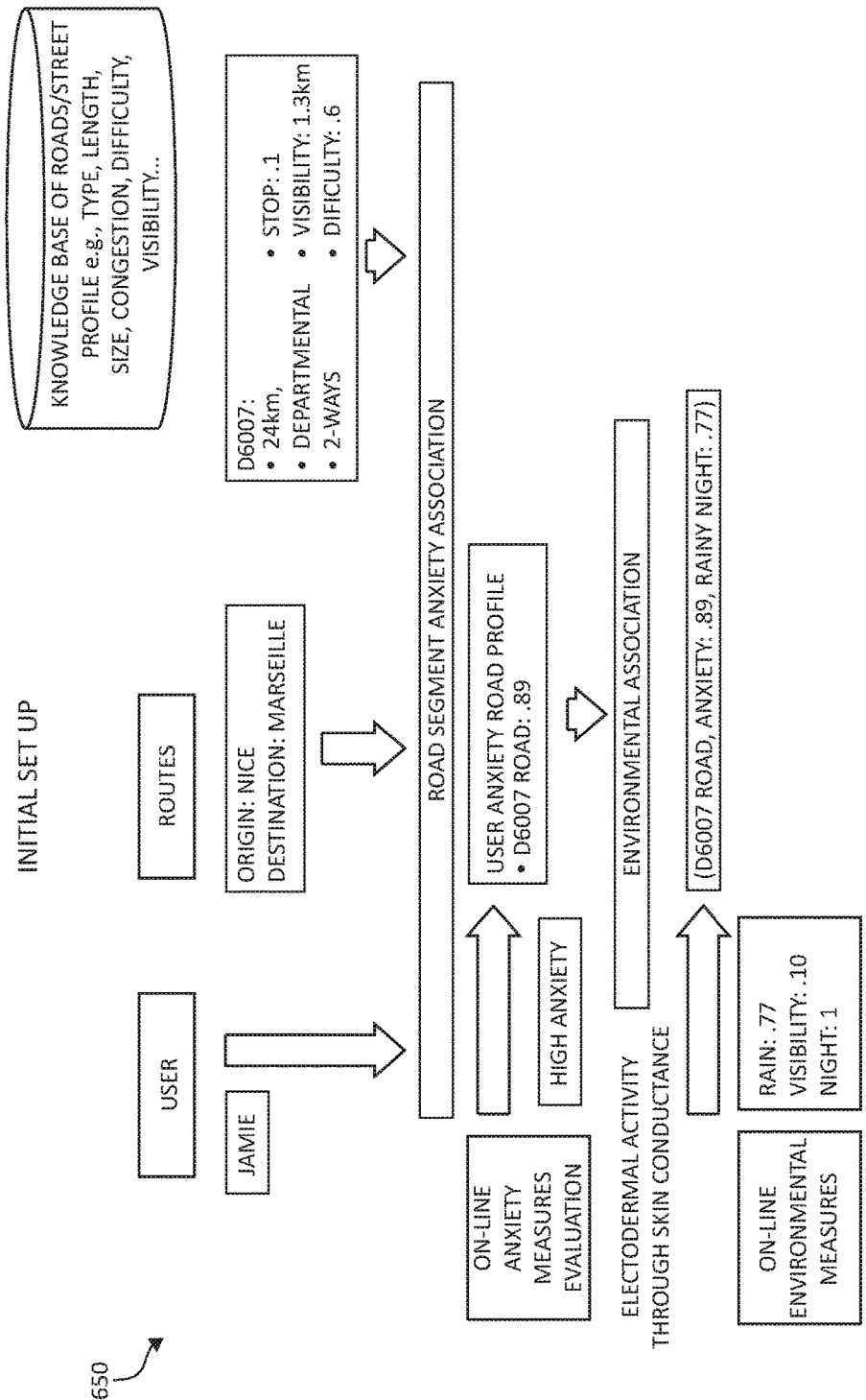
Figure 6D:
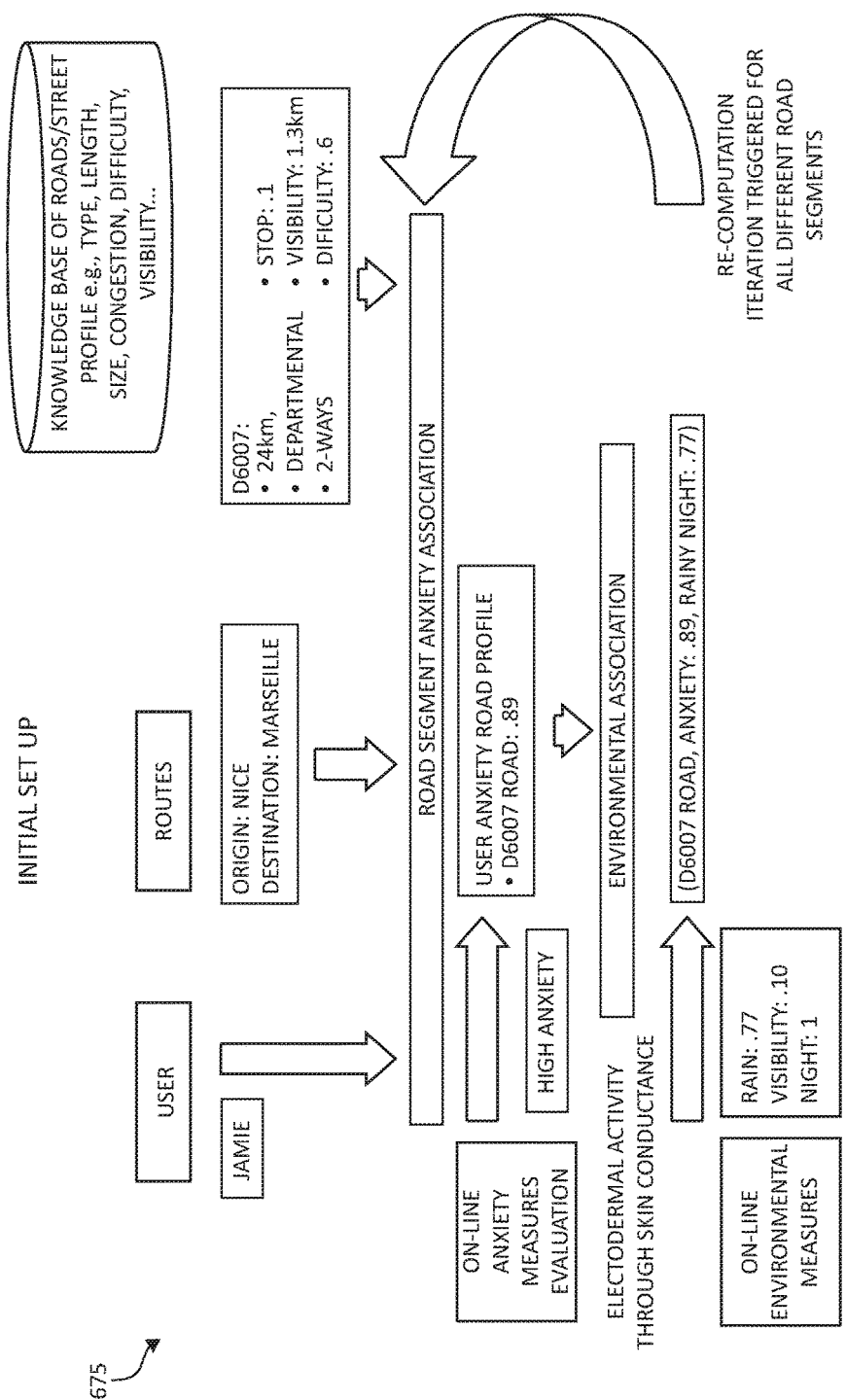
Figure 6E:
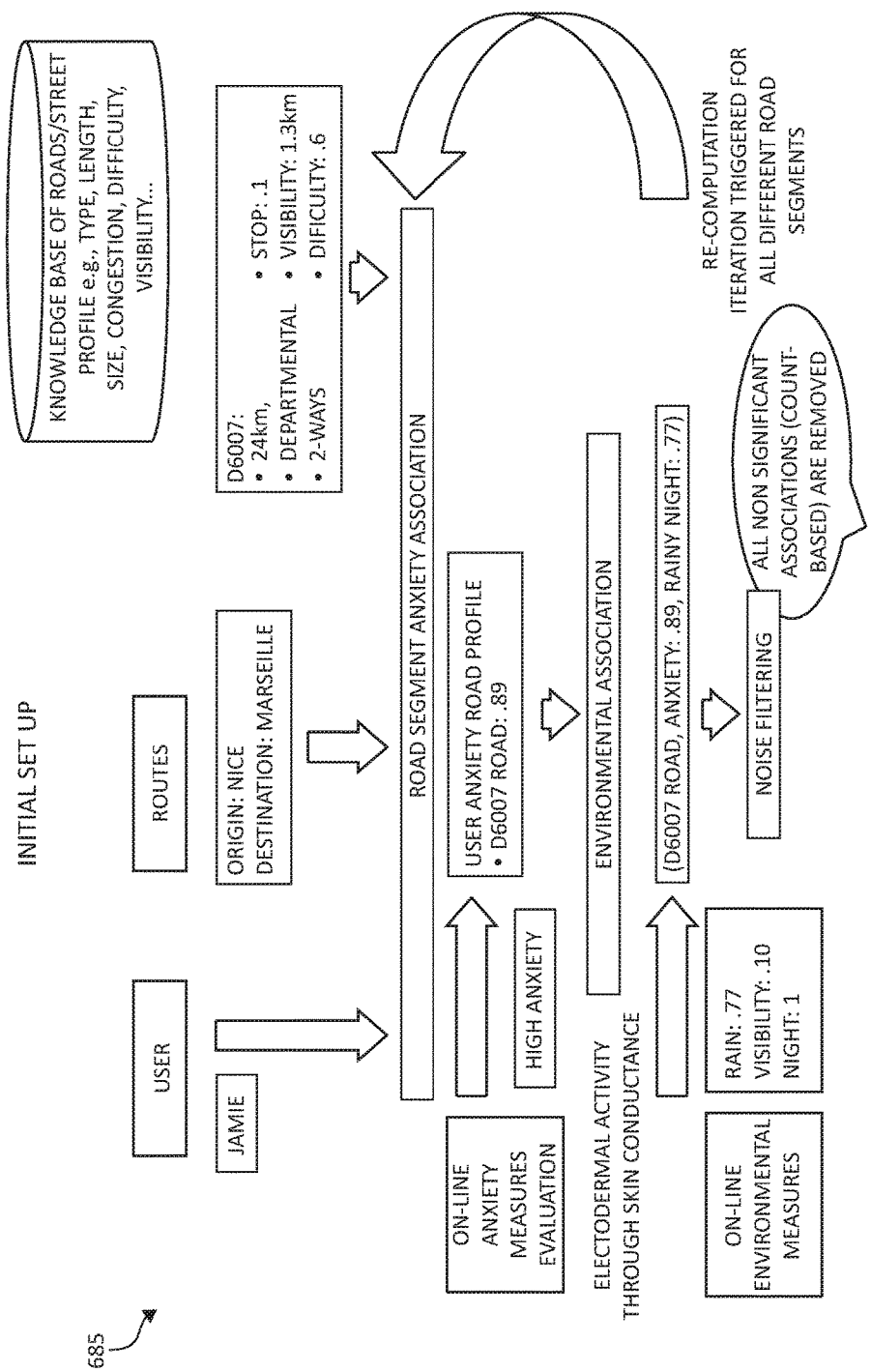
Figure 6F:
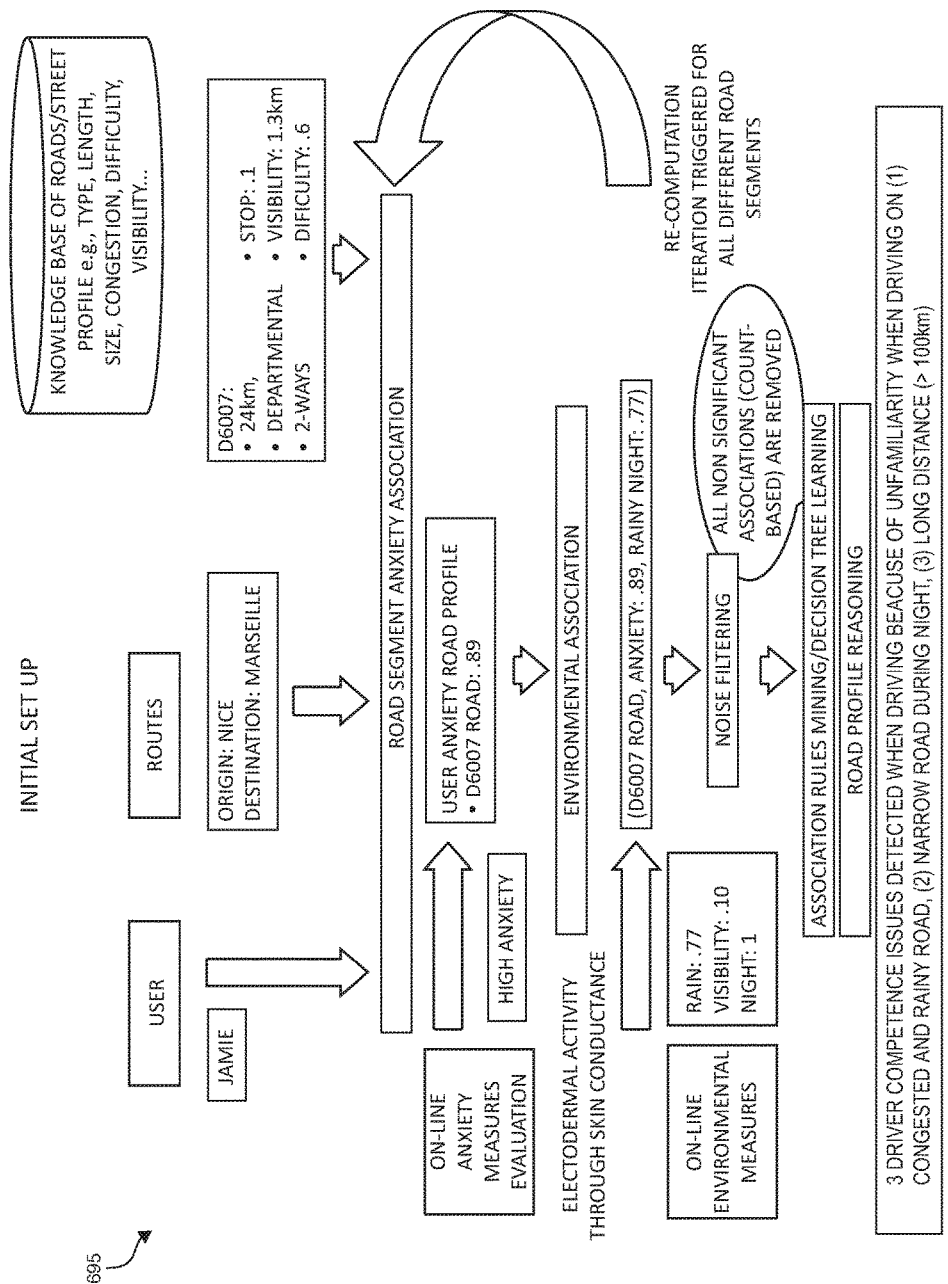

A first exemplary embodiment 600 of FIG. 6A, involves the configuration and initialization and set up for detection and handling of a particular driver competence (e.g., a driver named "Jamie"), one or more routes (e.g., the route for Jamie having an origin in "Nice, France" with the destination of "Marseille, France"). A route knowledge domain may include information and/or concepts relating to routes, roads, streets, highways, interstates, bridges, maps, and/or a variety of infrastructures relating to travel each having information relating to both size, length, a degree of complexity or difficulty (e.g., travel navigation complexity), visibility, problems or issues relating to road work or repair, and/or traffic congestion. For example, the knowledge domain for the route (identified as route D6007) from Nice, France, to Marseille, France has a distance of 24 kilometers (km), is a two-way road, classified as a departmental road, has at least one stop, has a visibility of at least 1.3 km, and has a degree of difficulty rated as 0.6. It should be noted that degree of difficulty of a route may be based on one or more factors, a governmental or traffic rating system, and/or a selected rating according to a third party, or other rating system relating to a route.

A second exemplary embodiment 625 (see FIG. 6B) involves the configuration and association of the user profile (e.g., data relating to the user/driver "Jamie"), the selected route, and the route knowledge domain for traveling from Nice, France to Marseille, France with measured driver anxiety (e.g., on-line anxiety measures evaluation—anxiety levels are captured in real-time by analyzing electro-dermal activity of drivers). In one aspect, the driver's anxiety may be measured using one or more sensors. In one aspect, the driver's anxiety may be measured using electro dermal activity through skin conductance (e.g., skin conductance or galvanic skin response may be captured through analysis of electro-dermal activity of drivers from the skin conductance and driver anxiety can be derived by comparing its level in different conditions, such as, for example at home, at work, and/or at sport. From this analysis a threshold of anxiety can be derived for each and every user). Based on the road segment anxiety association and correlation, the driver's anxiety (e.g., user anxiety road profile) may be calculated. For example, the driver Jamie has a user anxiety road profile for route D6007 as "0.89".

A third exemplary embodiment 650 (see FIG. 6C), involves the configuration and association of the user anxiety profile (e.g., for route D6007 as "0.89") with one or more environmental factors. In one aspect, the driver's anxiety may be correlated with environmental factors (e.g., on-line environmental measures) that may include the weather, route visibility, time of day and/or time of season. For example, the driver Jamie may be traveling on route D6007 in a rainy condition rated as "0.77", a route visibility of "0.10", and a time of day (e.g., night) rate of "1". Thus, the user anxiety profile is correlated with rainy conditions rated as "0.77", a route visibility of "0.10", and a time of day (e.g., night) rate of "1" (e.g., for route D6007, Anxiety: "0.89", Rainy Night: 0.77)

A fourth exemplary embodiment 675 (see FIG. 6D), a re-computation iteration operation may be triggered for each and every different road segment. The re-computation iteration operation for each and every different road segment may be related back to the road segment-anxiety association. It should be noted that the re-computation iteration triggered for each and every different road segment (and the arrow pointing back to the road segment anxiety association in FIG. 6D) is evaluating the anxiety level for each road segment. For example, consider a route from point A to point B, which may consist of a motorway section, a one way section, and a national road. In one aspect, it may not be desired to evaluate the overall anxiety level for the complete route from point A to point B, but instead, an evaluation is performed for determining the anxiety level of the driver to each different segment of the route. Therefore, an evaluation of the degree of confidence of the driver may be performed on any part of the route. In one aspect, an evaluation operation may be performed for the road segment-anxiety association anxiety level for each road segment (which depicts arrows back to the road segment anxiety association in FIG. 6D).

A fifth exemplary embodiment 685 (see FIG. 6E), involves the configuration and filtering (e.g., "noise filtering operation") of all non-significant associations (count based) with the user anxiety profile (e.g., for route D6007, Anxiety: "0.89", Rainy Night: 0.77). In one aspect, as pertaining to noise filtering and all non-significant associations (count based), the non-significant associations can be evaluated against a selected threshold. In essence, each and every association may have support and/or an indication which may indicate how many times a selected association has been observed. A threshold may be set up and noise filtering operation may be performed for all associations that do meet the threshold. The associations that do not meet the requirements of the threshold may be designated as the non-significant associations.

A sixth exemplary embodiment 695 (see FIG. 6F), decision tree learning and/or association rules mining operations may be used to generate road profile reasoning. That is the road profile reasoning may include an explanation for driver competence detection and evaluation. In one aspect, the explanation may include, for example, detecting a driver competence based on the road profile reasoning following the association rules mining/decision tree learning. For example, the driver competence detection and evaluation for Jamie may read "3 driver competence issues detected when driving because of unfamiliarity when driving on 1) a congested and rainy road, 2) a narrow road (D6007) during the night, and 3) a long distance (e.g., a distance greater than 100 km).

Figure 7:
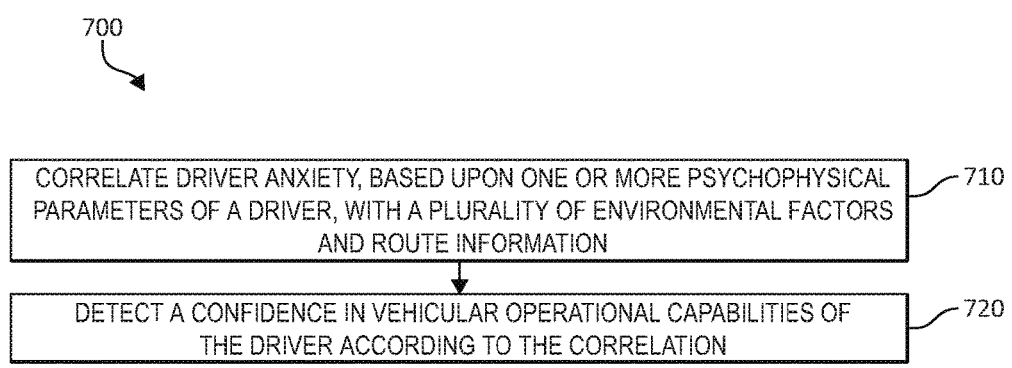
FIG. 7 is an additional flowchart diagram depicting an additional exemplary method for driver confidence evaluation while operating a vehicle, again in which various aspects of the present invention may be implemented.

Turning now to FIG. 7, a method 700 for driver competence evaluation while operating a vehicle by a processor is depicted, in which various aspects of the illustrated embodiments may be implemented. That is, FIG. 7 is a flowchart of an additional example method 700 for driver competence evaluation while operating a vehicle of a computing environment according to an example of the present technology. The functionality 700 may be implemented as a method executed as instructions on a machine, where the instructions are included on at least one computer readable medium or one non-transitory machine-readable storage medium. Starting in block 710, driver anxiety, based upon one or more psychophysical parameters of a driver, is correlated with a plurality of environmental factors and route information. A competence in vehicular operational capabilities of the driver may be detected according to the correlation, as in block 720. As one of ordinary skill in the art will appreciate, the various instrumentation for a vehicle may be used to measure and detect the one or more psychophysical parameters and also may depend on a variety of circumstances, such as resource constraints, importance to the manufacturer, buyer, or owner, or other factors.

In one aspect, in conjunction with and/or as part of at least one block of FIG. 7, the operations of method 700 may include each of the following. The operations of method 700 may monitor the one or more psychophysical parameters, wherein the one or more psychophysical parameters include at least a heart rate, blood pressure, or electro dermal activity. The operations of method 700 may also identify those of a plurality of routes associated with a current location of the driver or target destination as eligible routes matching the vehicular operational capabilities. The route information and the plurality of environmental factors may be analyzed according to a knowledge domain for the correlation. The data relating to the correlation may be stored in a driver profile for the driver. The driver anxiety may be detected or determined by comparing the one or more psychophysical parameters with a route associated with a current location of the vehicle or target destination and at least one of the plurality of environmental factors.

The operations of method 700 may also provide at least one suggestion to lower the driver anxiety or correct the competence in the vehicular operational capabilities (e.g., providing at least one suggestion to increase the driver confidence or correct the confidence in the vehicular operational capabilities) and/or provide customized travel routes for the driver to reduce the driver anxiety.

In view of the foregoing, the mechanisms of the present invention provide systems and methods for evaluating driver competence by correlating user anxiety (when driving) with external data such as road/street, traffic information, weather data, time (e.g., day/night). The detection of competence may be based on anxiety level (electro dermal activity, heart rate, blood pressure, and the like). An explanation provided may be based on correlation of anxiety and external data such as road, street, highway, traffic information, weather data, and/or time (e.g., day/night).

In one aspect, the mechanisms of the present invention automatically detect and explain driver competence which may be used for providing personalized recommendations of one or more routes, comparing drivers across different road segments, ensuring safe and secure travelling (if drivers avoid routes incompatible with a skill set of a driver), recommending targeted and personalized driving classes to improve vehicular operation skill sets.

In one aspect, the mechanisms of the present invention provide one or more benefits, such as, for example, enabling insurance companies to provide more efficient model risks (by charging more or less depending on driver behavior), enabling car rental companies to provide flexible prices to a driver (by charging more or less depending on driver behavior), assisting a driver to understand competency levels or skill levels, and anticipating travel risks, such as for an inexperienced driver traveling to an unfamiliar place. Moreover, communities and cities may provide more efficient urban planning with more efficient road infrastructures using data from drivers, and/or enabling driving schools to provide specific training targeted at increasing a driver's skill set.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method, by a processor, for driver competency evaluation while operating a vehicle, comprising:
    correlating driver confidence, based upon one or more psychophysical parameters of a driver, with a plurality of environmental factors and route information;
    detecting a competency in vehicular operational capabilities of the driver according to the correlation; wherein detecting the competency includes identifying an anxiety road profile value determined by measuring the one or more psychophysical parameters associated with the route information of a particular travel route; and
    performing one of a plurality of suggested confidence actions according to the detected competency to improve the vehicular operational capabilities through use of a user interface, thereby increasing driver safety while operating the vehicle; wherein performing one of the plurality of confidence actions further comprises performing at least one of:
providing at least one suggestion to increase the driver confidence or correct the confidence in the vehicular operational capabilities; and
providing customized travel routes for the driver to reduce the driver confidence.

2. The method of claim 1, further including monitoring the one or more psychophysical parameters, wherein the one or more psychophysical parameters include at least a heart rate, blood pressure, or electro dermal activity.

3. The method of claim 1, further including identifying a plurality of routes associated with a current location of the driver or target destination as eligible routes matching the vehicular operational capabilities.

4. The method of claim 1, further including analyzing the route information and the plurality of environmental factors according to a knowledge domain for the correlation, wherein data relating to the correlation is stored in a driver profile for the driver.

5. The method of claim 1, further including determining the driver confidence by comparing the one or more psychophysical parameters with a route associated with a current location of the vehicle or target destination and at least one of the plurality of environmental factors.

6. A system for driver confidence evaluation while operating a vehicle, comprising:
one or more computers with executable instructions that when executed cause the system to:
correlate driver confidence, based upon one or more psychophysical parameters of a driver, with a plurality of environmental factors and route information;
detect a competency in vehicular operational capabilities of the driver according
to the correlation; wherein detecting the competency includes identifying an anxiety road profile value determined by measuring the one or more psychophysical parameters associated with the route information of a particular travel route; and
perform one of a plurality of suggested confidence actions according to the detected competency to improve the vehicular operational capabilities through use of a user interface, thereby increasing driver safety while operating the vehicle; wherein performing one of the plurality of confidence actions further comprises performing at least one of:
providing at least one suggestion to increase the driver confidence or correct the confidence in the vehicular operational capabilities; and
providing customized travel routes for the driver to reduce the driver confidence.

7. The system of claim 6, wherein the executable instructions monitor the one or more psychophysical parameters, wherein the one or more psychophysical parameters include at least a heart rate, blood pressure, or electro dermal activity.

8. The system of claim 6, wherein the executable instructions identify a plurality of routes associated with a current location of the driver or target destination as eligible routes matching the vehicular operational capabilities.

9. The system of claim 6, wherein the executable instructions analyze the route information and the plurality of environmental factors according to a knowledge domain for the correlation, wherein data relating to the correlation is stored in a driver profile for the driver.

10. The system of claim 6, wherein the executable instructions determine the driver confidence by comparing the one or more psychophysical parameters with a route associated with a current location of the vehicle or target destination and at least one of the plurality of environmental factors.

11. A computer program product for driver confidence evaluation while operating a vehicle by a processor, the computer program product comprising a non-transitory computer-readable storage medium having computer-readable program code portions stored therein, the computer-readable program code portions comprising:
an executable portion that correlates driver competency, based upon one or more psychophysical parameters of a driver, with a plurality of environmental factors and route information;
an executable portion that detects a competency in vehicular operational capabilities of the driver according to the correlation; wherein detecting the competency includes identifying an anxiety road profile value determined by measuring the one or more psychophysical parameters associated with the route information of a particular travel route; and
an executable portion that performs one of a plurality of suggested confidence actions according to the detected competency to improve the vehicular operational capabilities through use of a user interface, thereby increasing driver safety while operating the vehicle; wherein performing one of the plurality of confidence actions further comprises performing at least one of:
providing at least one suggestion to increase the driver confidence or correct the confidence in the vehicular operational capabilities; and
providing customized travel routes for the driver to reduce the driver confidence.

12. The computer program product of claim 11, further including an executable portion that monitors the one or more psychophysical parameters, wherein the one or more psychophysical parameters include at least a heart rate, blood pressure, or electro dermal activity.

13. The computer program product of claim 11, further including an executable portion that identifies a plurality of routes associated with a current location of the driver or target destination as eligible routes matching the vehicular operational capabilities.

14. The computer program product of claim 11, further including an executable portion that analyzes the route information and the plurality of environmental factors according to a knowledge domain for the correlation, wherein data relating to the correlation is stored in a driver profile for the driver.

15. The computer program product of claim 11, further including an executable portion that determines the driver confidence by comparing the one or more psychophysical parameters with a route associated with a current location of the vehicle or target destination and at least one of the plurality of environmental factors.

* * * * *